US006180116B1

(12) United States Patent
Philippe et al.

(10) Patent No.: US 6,180,116 B1
(45) Date of Patent: Jan. 30, 2001

(54) HISTIDINE DERIVATIVES, PREPARATION PROCESS AND USES

(75) Inventors: Michel Philippe, Wissous; Thierry Bordier, Tremblay en France, both of (FR)

(73) Assignee: L'Oreal, Paris (FR)

( * ) Notice: Under 35 U.S.C. 154(b), the term of this patent shall be extended for 0 days.

(21) Appl. No.: 09/317,903

(22) Filed: May 25, 1999

(30) Foreign Application Priority Data

May 25, 1998 (FR) .................................................. 98 06538

(51) Int. Cl.$^7$ ...................................................... A61K 9/00
(52) U.S. Cl. .......................... 424/400; 424/401; 424/408; 424/409; 548/339.1
(58) Field of Search ..................................... 424/400, 401, 424/408, 409; 548/335.1, 339.1

(56) References Cited

FOREIGN PATENT DOCUMENTS

| 0 500 332 | 8/1992 | (EP) . |
| 2 668 365 | 4/1992 | (FR) . |
| WO 90 06102 | 6/1990 | (WO) . |

*Primary Examiner*—Dameron Jones
(74) *Attorney, Agent, or Firm*—Oblon, Spivak, McClelland, Maier & Neustadt, P.C.

(57) ABSTRACT

Histidine derivatives and processes of preparing the histidine derivatives. The histidine derivatives can be used to combat free radicals. The histidine derivatives may be used in cosmetic and/or dermatological compositions.

22 Claims, No Drawings

HISTIDINE DERIVATIVES, PREPARATION PROCESS AND USES

BACKGROUND OF THE INVENTION

1. Field of the Invention

The present invention relates to novel histidine derivatives and to processes of preparing the histidine derivatives. The present invention also relates to cosmetic or dermatological compositions containing these compounds. The compounds may be used as agents for combating free radicals.

2. Discussion of the Background

Sunlight, heat, atmospheric pollution and, in particular, smoke and tobacco are known to bring about the formation of free radicals. They mainly originate from molecular oxygen. Mention may be made of the following free radicals:

- singlet oxygen: highly oxidizing, highly toxic and with a very short lifetime, the product of the excitation of molecular oxygen by light photons;
- the superoxide radical anion: the product of the addition of an electron to oxygen, which can give rise to the production of highly reactive hydroxyl radicals;
- the hydroxyl radical: highly oxidizing and the most toxic to cells.

The formation of these radical species results in particular in the oxidation of cutaneous lipids. Living cells, in particular those of the skin, scalp and certain mucous membranes, are particularly sensitive to these free radicals, which is reflected by an accelerated ageing of the skin, with a complexion lacking radiance and premature formation of wrinkles or fine lines, and also by a decrease in the vigor and a lacklustre appearance of the hair. It is therefore particularly important to protect the skin, hair and mucous membranes from these free radicals. It is known that some antioxidants can inhibit the formation of free radicals. Thus, carnosine, or N-p-alanyl-L-histidine, which is a natural dipeptide found in the muscles of numerous vertebrates, is known for its activity in combating free radicals, in particular in combating singlet oxygen (E. Decker and H. Faraji, JAOCS, Vol. 67, No. 10, 650–652, 1990). Its use as an antioxidizing agent or as an agent for combating free radicals in cosmetics is described in WO-A-92/09298. However, carnosine exhibits problems of decomposition on contact with the skin, caused by enzymes present in the skin and in particular proteases, which results in a significant loss in its activity.

Histidine derivatives are also known, such as, for example, the derivatives N-(4-amino-1-oxobutyl)-L-histidine, -(5-amino-1-oxopentyl)-L-histidine and N-(6-amino-1-oxohexyl)-L-histidine disclosed in RU2084457. However, due to their physicochemical nature, these histidine derivatives are unsatisfactory in protecting non-polar compounds from oxidation.

Accordingly, there remains a need for compounds which are useful for combating free radicals.

SUMMARY OF THE INVENTION

It is an object of the present invention to provide compounds which combat free radicals with respect to oxidizable non-polar compounds and, in particular, effectively deactivate singlet oxygen.

It is another object of the invention to provide compositions containing the compounds which may be used for cosmetic and/or dermatological applications.

It is still another object of the invention to provide methods of making the compounds.

The present invention is based on the unexpected discovery that novel histidine derivatives exhibit excellent activity in combating free radicals with respect to oxidizable non-polar compounds and are highly effective in deactivating singlet oxygen. These compounds may, therefore, be used in cosmetics and in pharmaceuticals; they are readily applicable to the skin.

Accordingly, the object of the invention, and others, may be accomplished with novel histidine derivatives corresponding to the following general formula (I):

$$R'-X-[NH(CH)_{n'}-CO]_n-NH-CH-COO^-Q^+ \atop \phantom{R'-X-[NH(}R\phantom{H)_{n'}-CO]_n-NH-}CH_2-\text{imidazole}$$ (I)

where n is an integer ranging from 0 to 5, n' is an integer ranging from 1 to 16, R represents a side chain of an amino acid, X represents a radical chosen from the radicals of formulae, read from left to right:"

$-NH-CO-,\ -SO_2,\ -NH-CO-CO-,\ -O-CO-CO-,$

R' represents an optionally hydroxylated, saturated or unsaturated, linear or branched $C_6$ to $C_{22}$ alkyl radical or a $C_6$ to $C_{22}$ aminoalkyl radical, the amine functional group optionally being protected in the acetamide form or substituted by one or two lower alkyl groups, $Q^+$ represents $H^+$ or an organic or inorganic carton, or an addition salt of a compound of formula (I) with an organic or inorganic acid.

The objects of the invention may also be accomplished with a process for making the histidine derivatives.

The objects of the invention may also be accomplished with a composition comprising the histidine derivative as in a physiologically acceptable medium.

The objects of the invention may also be accomplished with a method of combating free radicals by applying the histidine derivatives to substrates to be protected against free radicals. In a preferred embodiment, the substrate may be skin and/or hair.

The objects of the invention may also be accomplished with a method of protecting a composition from free radicals by incorporating the histidine derivative into the composition.

A more complete appreciation of the invention and many of the attendant advantages thereof will be readily obtained as the same becomes better understood by reference to the following detailed description.

DETAILED DESCRIPTION OF THE INVENTION

The organic cation ($Q^+$) can be ammoniums comprising a residue chosen from basic amino acids, such as lysine or arginine, or from amino alcohols, such as glucamine, N-methylglucamine or 3-amino-1,2-propanediol. The inorganic cation ($Q^+$) can be chosen from alkali metal or alkaline earth metal cations, such as $Na^+$ or $K^+$, or $Q^+$ can be an $NH_4^+$ ion.

The addition salts with an acid may be chosen, for example, hydrochlorides, hydrobromides, sulphates, tartrates or acetates.

The compounds of formula (I) comprise at least one asymmetric carbon in their chemical structure. The invention relates both to the compounds with a D configuration or with an L configuration and to their mixtures, in particular a racemic mixture of the D and L compounds.

In the present invention, the preferred compounds of formula (I) satisfy at least one of the following:

(1) R' denotes a saturated, linear or branched alkyl radical having from 8 to 18 carbon atoms, (2) n is an integer from 1 to 5, and/or (3) n' is an integer ranging from 1 to 11.

In the present invention, preferable linear or branched alkyl radicals having from 6 to 22 carbon atoms include hexyl, octyl, nonyl, 2-ethylhexyl, dodecyl, hexadecyl and octadecyl radicals.

The lower alkyl groups generally comprise from 1 to 6 carbon atoms. For example, the lower alkyl group includes methyl, ethyl, propyl, iospropyl, tert-butyl and hexyl radicals.

Examples of linear alkyl radicals having from 6 to 22 carbon atoms include the octyl, dodecyl, hexadecyl and octadecyl radicals.

Examples of the branched alkyl radicals having from 6 to 22 carbon atoms include 2-methylpentyl, 1-methylhexyl and 3-methylheptyl radicals. "Unsaturated alkyl radical" is preferably understood to mean a linear or branched radical having from 6 to 22 carbon atoms and comprising one or more double bonds.

The side chains of an amino acid correspond to the side chains of any one of the natural amino acids. The identity of the side chains of the natural amino acid side chains is described in L. Stryer, *Biochemistry*, Third Edition, incorporated herein by reference in its entirety. Thus, R can represent in particular hydrogen or a methyl or isopropyl radical. R can therefore be nonpolar, polar but uncharged, or negatively or positively charged side chains.

Examples of the preferred compounds corresponding to the general formula (1) include:

N-octylaminocarbonyl-β-alanyl-L-histidine,

N-dodecylaminocarbonyl-β-alanyl-L-histidine,

N-octylsulphonyl-β-alanyl-L-histidine,

N-dodecylsulphonyl-β-alanyl-L-histidine, and

N-dodecylaminooxalyl-β-alanyl-L-histidine.

Another subject-matter of the present invention is a process for the preparation of the compounds of formula (I). This process comprises the reaction with histidine in an inert solvent of a compound of formula (II)

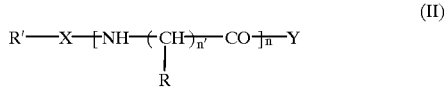

(II)

in which n', n, R, R' and X have the same meanings as in the above formula (I), and Y is a conventional activating group for the acidic functional group.

Reactions for the activating the —COOH acidic groups are well known to those skilled in the art. Reference may be made, for example, to *Advanced Organic Chemistry*, Jerry March, 3rd Edition, 1985, pp. 370–377, incorporated herein by reference. "Coupling agent" is understood to mean any compound which can substitute the OH group of the compound of formula (IV) and then be substituted subsequently by the amino acid which it is desired to graft, for example histidine. Coupling agents are described in *Advanced Organic Chemistry*, J. March. 3rd Edition, 1985, p. 372, incorporated herein by reference. A particularly preferred coupling agent is 2-(5-norbomene-2,3-dicarboximido)-1,1,3,3-tetramethylammonium tetrafluoroborate.

The starting histidine, comprising an asymmetric carbon, is used in the pure optical form or in the mixed optical form (D; L; D, L), depending on the desired optical form of the compound of formula (I).

Examples of the solvent include dichloromethane, 1,2-dichloroethane, 1,1,1-trichloroethane, chloroform, acetonitrile, toluene, dioxane, tetrahydrofuran, 1,2-dimethoxyethane, cyclohexane, dimethylformamide, water or a mixture of these solvents.

The reaction is carried out at a temperature preferably of between −10° C. and +40° C. and more preferably between 20° C. and 30° C.

The reaction can be carried out in the presence of a base. The base may be chosen from alkali metal or alkaline earth metal hydroxides, sodium hydrogen carbonate, alkali metal alkoxides, alkaline hydrides or tertiary amines, such as pyridine, diisopropylechylamine or triethylamine. Sodium hydrogen carbonate is a preferred base.

Another subject-matter of the present invention is a composition comprising, in a physiologically acceptable medium, a compound of formula (I) as defined above. The composition comprising the compound can be provided in particular in the form of a cosmetic or pharmaceutical composition respectively comprising a cosmetically or pharmaceutically acceptable medium. In the compositions according to the invention, the compounds of formula (I) are generally present at a concentration of 0.001% to 15% by weight and preferably of 0.01% to 5% by weight with respect to the total weight of the composition. These weight % ranges include all specific values and subranges therebetween, including 0.005, 0.02, 0.05, 1, 2, 8, 10 and 12% by weight.

These compositions can be prepared according to the usual methods known to a person skilled in the art. They can be in the form of a lotion, gel, water-in-oil or oil-in-water emulsion, microemulsion, milk or cream, powder, paste, solid stick, spray or aerosol foam.

Another subject-matter of the invention is the use of the compounds of formula (I) as agent for combating free radicals and in particular as agent for combating free radicals which deactivates singlet oxygen, in particular in a cosmetic or pharmaceutical composition.

The invention also relates to the use of the compounds of formula (I) in a cosmetic or pharmaceutical composition for the treatment of keratinous substances against the effects of ageing. "Keratinous substances" is understood to mean the skin, hair, nails, body hairs, mucous membranes and semi-mucous membranes, such as the lips.

The compounds of formula (I) constitute anionic amphiphilic lipids which can be included in a vesicular system.

The compositions comprising the compounds according to the invention can also comprise, in a known way, one or more active compounds having a cosmetic and/or pharmaceutical activity which, depending on their solubility characteristics, can be located in different places. For example, in the case of dispersions of vesicles comprising an encapsulated aqueous phase, it the active principles are fat-soluble, they can be present in the lipid phase constituting the layer(s) of the vesicles or in the droplets of waterimmiscible liquid stabilized by the vesicles. If the active principles are water-soluble, they can be present in the encapsulated aqueous phase of the vesicles or in the continuous aqueous phase of the dispersion. If the active principles are amphiphilic, they are distributed between the lipid phase and the encapsulated aqueous phase with a partition coefficient which varies according to the nature of the amphiphilic active principle and the respective compositions of the lipid phase and of the encapsulated aqueous phase. The active principles are generally positioned in the lipid phase of the layers and/or in the phase encapsulated by the layers.

The compositions according to the invention to may also comprise, formulation additives having neither a cosmetic activity nor a pharmaceutical activity of their own but which are of use in the formulation of the compositions. Mention may be made, among these additives, for example, of gelling agents, polymers, preservatives, colorants, opacifiers and fragrances.

The cosmetic or pharmaceutical compositions according to the invention may be provided, for example, in the form of shampoos or conditioners, of cleansing compositions, of creams for caring for the skin or hair, of antisun compositions, of shaving creams or foams, of body deodorants, of compositions for oral use, of hair dyeing compositions or of make up compositions, for example.

The histidine derivatives of the present invention may be used to protect substrates against free radicals. Here, an effective amount of the histidine derivative(s) is applied to the substrate. Suitable substrates include skin and hair.

The histidine derivatives of the present invention may be used to protect compositions against the effects of free radicals. An effective amount of the histidine derivative(s) is incorporated into the compositions. For example, the composition may contain 0.001% to 15% by weight of the histidine derivative(s).

Having generally described this invention, a further understanding can be obtained by reference to certain specific examples which are provided herein for purposes of illustration only and are not intended to be limiting unless otherwise specified.

EXAMPLES

Example 1

N-Octylsulphonyl-β-alanyl-L-histidine a) Synthesis of N-octylsulphonyl-β-alanine 2 g (22.45 mmol) of P-alanine are dissolved in 1 equivalent of 1N sodium hydroxide solution in a three-necked flask equipped with two 250 ml dropping funnels and with a glass electrode for measuring the pH. 1 equivalent of 1-octanesulphonyl chloride in tetrahydrofuran is introduced dropwise into the reaction mixture at room temperature. The pH is maintained above 9 by the simultaneous addition of 1 equivalent of 1N sodium hydroxide solution. After stirring for 3 hours at room temperature, the mixture is acidified with approximately 1.1 equivalents of a 3N hydrochloric acid solution. The heterogeneous mixture is extracted with 100 ml of ethyl acetate. The organic phase is washed with 3 times 20 ml of water, dried over sodium sulphate and then evaporated to dryness. The solid residue is taken up in heptane and is then filtered off and dried under vacuum. 1.6 g of a white product are obtained, i.e. a yield of 30%.

Melting point: 121.8° C. (Mettler FPR9)

Elemental analysis ($C_{11}H_2NO_4S$, MW=265.372)

|  | C | H | N | O | S |
| --- | --- | --- | --- | --- | --- |
| % calculated | 49.79 | 8.74 | 5.28 | 24.12 | 12.08 |
| % found | 49.72 | 8.76 | 5.24 | 24.18 | 12.10 | b) Synthesis of N-octylsulphonyl-β-alanyl-L-histidine 4 g (15 07 mmol) of N-octylenlphonyl-β-alanine are dissolved in 50 ml of tetrahydrofuran and 1 equivalent of triethylamine in a 100 ml three-necked flask equipped with a thermometer and with a 10 ml dropping funnel. 1 equivalent of pivaloyl chloride is then introduced at a temperature of 5° C. The mixture is 12 subsequently stirred for 1 hour at a temperature of 20° C. A solution comprising 1.2 equivalents of histidine and 1.2 equivalents of sodium hydroxide in 20 ml of water is prepared and then run dropwise into the reaction mixture while maintaining the temperature below 30° C. After stirring for 6 hours, the mixture is neutralized with 1 equivalent of SN hydrochloric acid. The solvent is evaporated and then 50 ml of water are introduced. The precipitate is filtered off, washed with water and then dried under vacuum over phosphorus pentoxide. The crude product is washed with acetone and then recrystallized from 95° ethanol. 1.6 g of a white product are obtained, i.e. a yield of 27%.

Analyses

Melting point: 146.8° C. (Mettler FP89)

Thin layer chromatography ($SiO_2$), eluent $NH_4OH$ 6/$CH_3OH$ 47/$CH_2Cl_2$ 47: $R_f$=0.74 (iodine visualization)

Elemental analysis ($C_{17}H_{30}N_4O_5S$, MW=402.513)

|  | C | H | N | O | S |
| --- | --- | --- | --- | --- | --- |
| % calculated | 50.73 | 7.51 | 13.92 | 19.87 | 7.97 |
| % found | 50.41 | 7.98 | 10.61 | 21.19 | 9.44 |

Example 2

N-Octylaminocarbonyl-β-alanyl-L-histidine a) Synthesis of N-octylaminocarbonyl-β-alanine 4 g (24.67 mmol) of 1,1'-carbonyldiimidazole are dissolved in 40 ml of dimethylformamide in a 100 ml three-necked flask under a nitrogen atmosphere. 4 g (24.67 mmol) of octylamine are then introduced. After stirring for 45 minutes at room temperature, a solution of 2.4 g (1.1 equivalents) of P-alanine in 10 ml of aqueous sodium hydroxide solution (1.1 equivalents) is added dropwise to the preceding mixture. The mixture becomes heterogeneous, which mixture is subsequently neutralized with a concentrated hydrochloric acid solution diluted by half. The precipitate is filtered off, washed with water and then dried under vacuum over phosphorus pentoxide. 4.9 g of a white product are obtained, i.e. a yield of 82%.

Analyses:

Melting point: 136.9° C. (Mettler FPB9)

Elemental analysis ($C_{12}H_{24}N_2O_3$, MW=244.333)

|  | C | H | N | O |
|---|---|---|---|---|
| % calculated | 58.99 | 9.9 | 11.47 | 19.64 |
| % found | 58.82 | 9.96 | 11.12 | 19.61 | b) Synthesis of N-octylaminocarbonyl-β-alanyl-L-histidine 3 g (12.28 mmol) of N-octylaminocarbonyl-β-alanine are dissolved in 60 ml of tetrahydrofuran and 1 equivalent of triethylamine in a 100 ml three-necked flask equipped with a thermometer and with a 10 ml dropping funnel. 1 equivalent of pivaloyl chloride is then introduced at a temperature of 5° C. The mixture is subsequently stirred for 1 hour at a temperature of 20° C. A solution comprising 1.2 equivalents of histidine and 1.2 equivalents of sodium hydroxide in 20 ml of water is prepared and then run dropwise into the reaction mixture while maintaining the temperature below 30° C. After stirring for 6 hours, the mixture is neutralized with 1 equivalent of 5 N hydrochloric acid. The solvent is evaporated and then 50 ml of water are introduced. The precipitate is filtered off, washed with water and then dried under vacuum over phosphorus pentoxide. The crude product is washed with acetone and then recrystallized from 95° ethanol. 1.4 g of a white product are obtained, i.e. a yield of 30%.

Analyses:

Melting point: 199.6° C. (Mettler FP89)

Thin layer chromatography ($SiO_2$), eluent $NH_4OH$ 6/$CH_3OH$ 47/$CH_2Cl_2$ 47: $R_f$=0.82 (iodine visualization).

Elemental analysis ($C_{18}H_{31}N_5O_4$, MW=381.474)

|  | C | H | N | O |
|---|---|---|---|---|
| % calculated | 56.68 | 8.19 | 18.36 | 16.78 |
| % found | 54.41 | 8.19 | 17.09 | 17.96 |

Obviously, numerous modifications and variations of the present invention are possible in light of the above teachings. It is therefore to be understood that within the scope of the appended claims, the invention may be practiced otherwise than as specifically described herein.

This application is based on French Patent Application Serial No. 98-06538, filed on May 25, 1998, and incorporated herein by reference.

What is claimed is:

1. A histidine derivative represented by the formula (I):

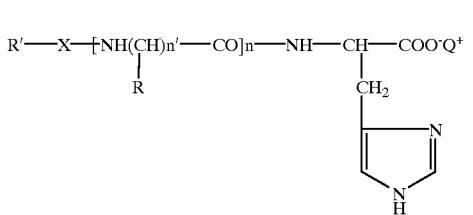

wherein
n is an integer from 0 to 5,
n' is an integer from 1 to 16,
R represents a side chain of an amino acid,
X represents a radical, selected from the group consisting of —NH—CO—, —SO$_2$—, —NH—CO—CO—, and —O—CO—CO—,
R' represents an optionally hydroxylated, saturated or unsaturated, linear or branched $C_6$ to $C_{22}$ alkyl radical or a $C_6$ to $C_{22}$ aminoalkyl radical, wherein the amine functional group of the $C_6$ to $C_{22}$ aminoalkyl radical is optionally protected as an acetamide or is substituted by one or two lower alkyl groups, and
$Q^+$ represents $H^+$ or an organic or inorganic cation,
or an addition salt of a histidine derivative represented by the formula (I) with an organic or inorganic acid.

2. The histidine derivative of claim 1, wherein the organic cation is selected from ammoniums comprising basic amino acids or amino alcohols.

3. The histidine derivative of claim 1, wherein the inorganic cation is selected from the group consisting of alkali metal cations, alkaline earth metal cations, and $NH_4^+$.

4. The histidine derivative of claim 1, which is an addition salt selected from the group consisting of hydrochlorides, hydrobromides, sulphates, tartrates, and acetates.

5. The histidine derivative of claim 1, which has at least one of the following characteristics:
(1) R'0 represents a saturated, linear or branched alkyl radical having from 8 to 18 carbon atoms,
(2) n is an integer from 1 to 5, or
(3) n' is an integer from 1 to 11.

6. The histidine derivative of claim 1, which is selected from the group consisting of N-octylaminocarbonyl-β-alanyl-L-histidine, N-dodecylaminocarbonyl-β-alanyl, L-histidine, N-octylsulphonyl-β-alanyl-L-histidine, N-dodecylsulphonyl-β-alanyl-L-histidine, and N-dodecylaminooxalyl-β-alanyl-L-histidine.

7. The histidine derivative of claim 1, which is said addition salt.

8. The histidine derivative of claim 1, wherein X is —NH—CO—.

9. The histidine derivative of claim 1, wherein X is —SO$_2$—.

10. The histidine derivative of claim 1, wherein X is —NH—CO—CO—.

11. The histidine derivative of claim 1, wherein X is —O—CO—CO—.

12. The histidine derivative of claim 1, wherein R' represents a saturated or unsaturated, linear or branched $C_6$ to $C_{22}$ alkyl radical.

13. The histidine derivative of claim 1, wherein R' represents a saturated or unsaturated, linear or branched $C_6$ to $C_{22}$ aminoalkyl radical.

14. A composition, comprising, in a physiologically acceptable medium, at least one histidine derivative as defined in claim 1.

15. The composition of claim 14, which is in the form of a cosmetic or pharmaceutical composition.

16. A composition of claim 14, which is in the form of a lotion, gel, emulsion, microemulsion, milk or cream, powder, paste, solid stick, spray or aerosol foam.

17. The composition of claim 14, comprising 0.001% to 15% by weight of the histidine derivative.

18. The composition of claim 14, comprising 0.005% to 5% by weight of the histidine.

19. A method of combating free radicals, comprising applying the histidine derivative of claim 1 to a substrate to be protected against free radicals.

20. The method of claim 19, wherein the substrate is skin and/or hair.

21. A method of protecting a composition from free radicals, comprising incorporating the histidine derivative of claim 1 into the composition.

22. A process for preparing histidine derivatives represented by formula (I):

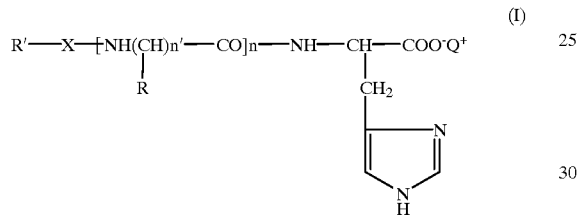

wherein n is an integer ranging from 0 to 5, n' is an integer ranging from 1 to 16, R represents a side chain of an amino acid, X represents a radical, selected from the group consisting of —NH—CO—, —SO$_2$—, —NH—CO—CO—, and —O—CO—CO—, R' represents an optionally hydroxylated, saturated or unsaturated, linear or branched $C_6$ to $C_{22}$ alkyl radical or a $C_6$ to $C_{22}$ aminoalkyl radical, wherein the amine functional group of the $C_6$ to $C_{22}$ aminoalkyl radical is optionally protected as an acetamide or is substituted by one or two lower alkyl groups, and Q$^+$ represents H$^+$ or an organic or inorganic cation, or an addition salts of a histidine derivative represented by formula (I) with an organic or inorganic acid, comprising:

reacting histidine, in an inert solvent, with a compound represented by formula (II)

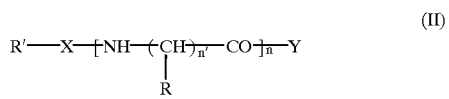

wherein n', n, R, R' and X are as defined above, and

Y is a group which activates the acidic functional group.

* * * * *

UNITED STATES PATENT AND TRADEMARK OFFICE
CERTIFICATE OF CORRECTION

PATENT NO. : 6,180,116 B1
DATED : January 30, 2001
INVENTOR(S) : PHILIPPE et al.

It is certified that error appears in the above-identified patent and that said Letters Patent is hereby corrected as shown below:

Column 8, line 42, "R'0" should read --R'--.

Signed and Sealed this

Fifteenth Day of May, 2001

Attest:

NICHOLAS P. GODICI

Attesting Officer      Acting Director of the United States Patent and Trademark Office